(12) United States Patent
Mayer et al.

(10) Patent No.: US 7,452,540 B2
(45) Date of Patent: Nov. 18, 2008

(54) ENHANCED IMMUNIZATION AND SUPPRESSION OF ORAL TOLERANCE

(75) Inventors: Lloyd Mayer, Kings Point, NY (US); Clifford P. Stanners, Picton (CA)

(73) Assignees: Mount Sinai School of Medicine, New York, NY (US); McGill University, Montreal, Quebec (CA)

( * ) Notice: Subject to any disclaimer, the term of this patent is extended or adjusted under 35 U.S.C. 154(b) by 260 days.

(21) Appl. No.: 10/492,571

(22) PCT Filed: Oct. 15, 2002

(86) PCT No.: PCT/US02/32733

§ 371 (c)(1),
(2), (4) Date: Aug. 23, 2004

(87) PCT Pub. No.: WO03/070266

PCT Pub. Date: Aug. 28, 2003

(65) Prior Publication Data

US 2005/0053613 A1    Mar. 10, 2005

(51) Int. Cl.
*A61K 39/00* (2006.01)
*C07K 16/00* (2006.01)

(52) U.S. Cl. ............. 424/184.1; 424/185.1; 424/277.1; 514/12

(58) Field of Classification Search ............... None
See application file for complete search history.

(56) References Cited

U.S. PATENT DOCUMENTS 6,852,320 B2 *   2/2005   Blumberg ................ 424/133.1

2003/0022292 A1 *   1/2003   Gray-Owen et al. ....... 435/69.1

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Taheri et al JBC vol. 275 p. 26935-26943 (2000).*
Amalfitano et al. (Current Gene Therapy 2002, 2: 111-133).*
The Department of Health and Human Services has released a memorandum dated Jan. 14, 2003.*

* cited by examiner

*Primary Examiner*—Sheela J Huff
(74) *Attorney, Agent, or Firm*—Klauber & Jackson LLC

(57) ABSTRACT

This invention provides for methods of immunizing mammals against tumors expressing a carcinoembryonic antigen using a carcinoembryonic immunogen modified to lack cellular immunosuppressive activity or CD1d binding. The invention further provides for use of a carcinoembryonic immunogen having a region recognized by antibody B9 or L12 modified to inactivate cellular immunosuppressive activity. Methods are also provided for modifying the immunogen by deleting, altering, mutating or truncating the immunosuppressive region. The invention also provides for enhancing cellular immunogenicity of an orally delivered immunogen by co-administration of an agent capable of inhibiting the immunosuppressive activity of carcinoembryonic antigen. Further methods are provided for creating a patient having a carcinoembryonic-antigen-family-member-expressing tumor by immunizing the patient with the carcinoembryonic-antigen-family-member lacking the immunosuppressive region. Pharmaceutical compositions for eliciting an effective immune response to the carcinoembryonic antigen are also provided.

10 Claims, 13 Drawing Sheets

Figure 1  Sequence Analysis

LTIESTPFNVAEGK          LLLVHNLPQX X(L/G)F

>gi|11386171|ref|NP_004354.1| carcinoembryonic antigen-related cell adhesion molecule 5; carcinoembryonic antigen [Homo sapiens]
gi|115940|sp|P06731|CCEM_HUMAN CARCINOEMBRYONIC ANTIGEN PRECURSOR (CEA) (MECONIUM ANTIGEN 100)
   (CD66E ANTIGEN)
gi|87039|pir||A36319 carcinoembryonic antigen precursor - human
gi|178677|gb|AAB59513.1| (M17303) carcinoembryonic antigen precursor [Homo sapiens]
gi|180223|gb|AAA51967.1| (M29540) carcinoembryonic antigen [Homo sapiens]
   Length = 702

Score = 45.9 bits (108), Expect = 7e-05
Identities = 25/28 (89%), Positives = 25/28 (89%), Gaps = 2/28 (7%)

Query:  1  LTIESTPFNVAEGK--  LLLVHNLPQXLF 26
           LTIESTPFNVAEGK    LLLVHNLPQ  LF
Sbjct: 36  LTIESTPFNVAEGKEVLLLVHNLPQHLF 63

Phoenix/CEA-GFP; B9
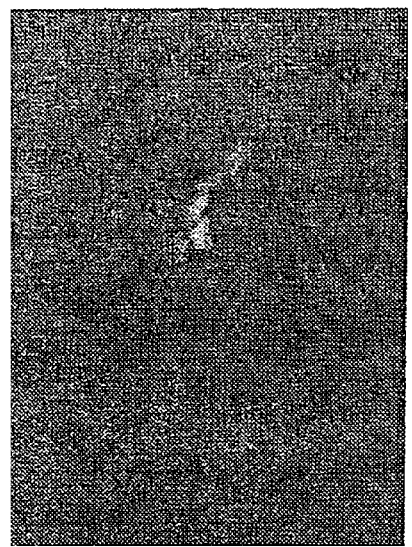
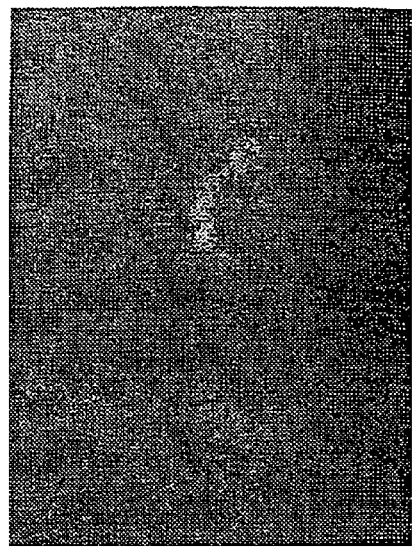
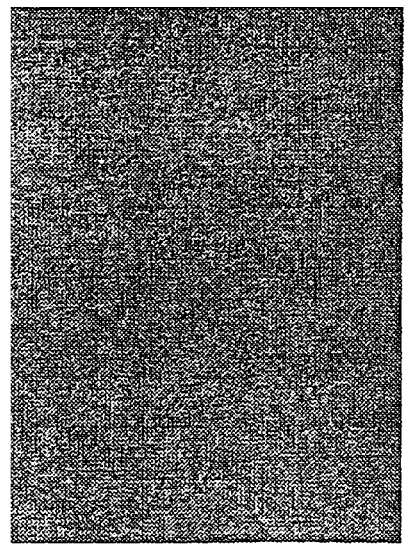
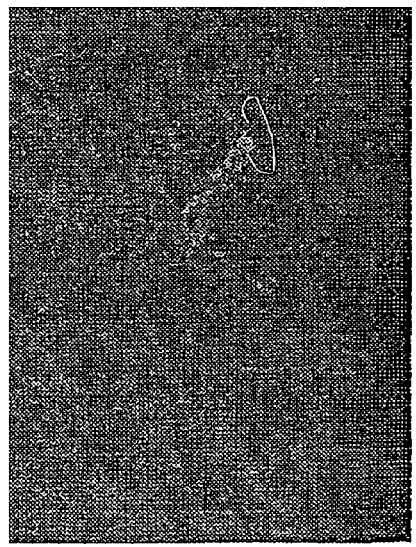
phase — GFP
B9 — co-localize
Fig 2

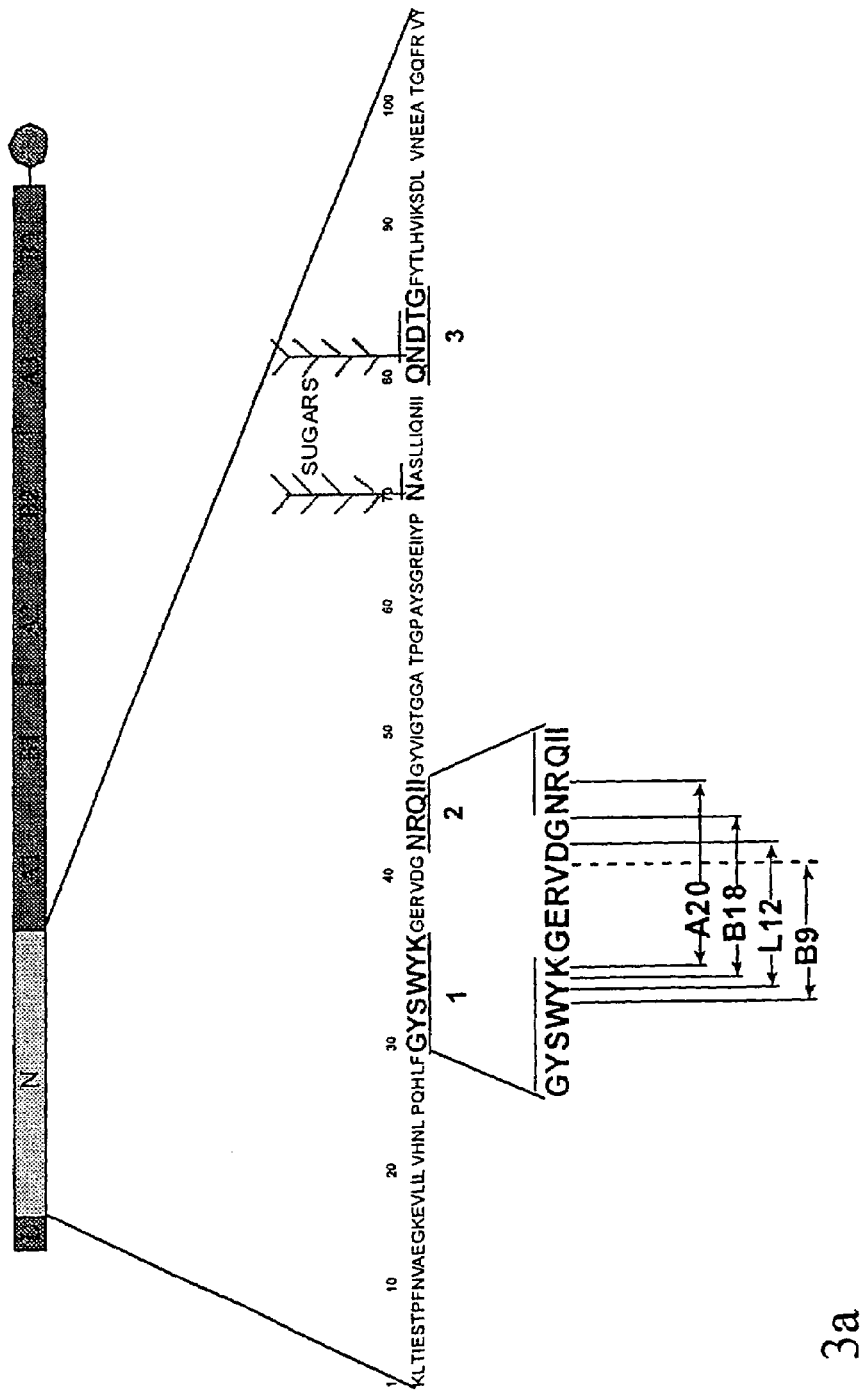

Staining of CEA subfamily transfectants with anti-CEA mAbs

| Family | B9 | B18 | A20 |
|---|---|---|---|
| CEA | ++ | ++ | ++ |
| NCA (CC 6) | + | + | - |
| BGPa (CC 1-42) | + | - | + |
| CGM 6 (CC 8) | +/- | - | - |
| CGM 2 (CC 7) | - | - | - |
| BGPx (CC 1-11) | ++ | ++ | - |

Fig 5B

SEQUENCE LISTING

```
<160> NUMBER OF SEQ ID NOS: 3

<210> SEQ ID NO 1
<211> LENGTH: 17
<212> TYPE: PRT
<213> ORGANISM: Artificial Sequence
<220> FEATURE:
<223> OTHER INFORMATION: synthetic fragment of carcinoembryonic antigen
      from homo sapiens

<400> SEQUENCE: 1

Gly Tyr Ser Trp Tyr Lys Gly Glu Arg Val Asp Gly Asn Arg Gln Ile
 1               5                   10                  15
```

```
Ile

<210> SEQ ID NO 2
<211> LENGTH: 7
<212> TYPE: PRT
<213> ORGANISM: Artificial Sequence
<220> FEATURE:
<223> OTHER INFORMATION: synthetic fragment of carcinoembryonic antigen
      from homo sapiens

<400> SEQUENCE: 2

Trp Tyr Lys Gly Glu Arg Val
 1               5

<210> SEQ ID NO 3
<211> LENGTH: 7
<212> TYPE: PRT
<213> ORGANISM: Artificial Sequence
<220> FEATURE:
<223> OTHER INFORMATION: synthetic fragment of carcinoembryonic antigen
      from homo sapiens

<400> SEQUENCE: 3

Tyr Lys Gly Glu Arg Val Asp
 1               5
```

ENHANCED IMMUNIZATION AND SUPPRESSION OF ORAL TOLERANCE

FIELD OF THE INVENTION

This invention relates to methods for immunizing mammals against tumors expressing a carcinoembryonic antigen by immunizing the mammal with a carcinoembryonic antigen that has been modified to lack immunosuppressive activity. The invention further relates to enhancement of cellular immunogenicity of orally-delivered immunogens by co-administration of the immunogen with agents capable of inhibiting the immunosuppressive activity of carcinoembryonic antigen, methods of treating patients having a carcinoembryonic antigen family member expressing tumor, and pharmaceutical compositions for effectively eliciting an immune response to a carcinoembryonic antigen family member.

BACKGROUND OF THE INVENTION

The nature of the immune response in the intestine is one of suppression or controlled inflammation. Several groups have suggested that this type of response is dictated by the nature of the microenvironment in which the mucosa-associated lymphoid tissue resides. Several factors come into play to promote this suppressed state: regulatory T cells, poorly reactive macrophages, unusual T lymphocyte populations (intraepithelial and lamina propria lymphocytes) and unique antigen presenting cells. Included in this later population are intestinal epithelial cells. Evidence has been provided for such functional properties in both rat, mouse and man. In rat and man, antigens presented by these cells result in the selective activation of $CD8^+$ suppressor T cells.

Two cell surface molecules involved in this interaction have been identified: the nonclassical class I molecule CD1d and a surface glycoprotein recognized by two anti-epithelial cell monoclonal antibodies (mAbs), B9 and L12, called gp180. These two mAbs block the selective proliferation of $CD8^+$ T cells and inhibit the phosphorylation of the CD8 associated kinase p56 l ck in IEC: T cell co-cultures. Purified gp180 (mAb B9 affinity purified material) binds to CD8, activates p56 l ck and forms a complex with CD1d.

It is towards the identification and further characterization of gp180 and its exploitation for immunomodulatory purposes that the present invention is directed.

SUMMARY OF THE INVENTION

In a first aspect, the present invention is directed to a method for effectively immunizing an animal against a carcinoembryonic-antigen-family-member-expressing tumor by at least immunizing the animal using an immunogen consisting of a carcinoembryonic antigen family member lacking cellular immunosuppressive activity. The carcinoembryonic antigen family member lacking cellular immunosuppressive activity may be a carcinoembryonic antigen (CEA) family member which has an alteration or deletion of a region that is recognized by monoclonal antibody B9, or it may be GYSW-YKGERVDGNRQII (SEQ ID NO:1), WYKGERV (SEQ ID NO:2) or YKGERVD (SEQ ID NO:3). The lacking of the cellular immunosuppressive region or activity may be achieved by altering, deleting, replacing, or otherwise modifying one or more amino acids in the cellular immunosuppressive region of the CEA family member molecule, such that the altered protein lacks the ability to suppress an immune response or induce suppressor T cells capable of suppressing an immune response. The suppression may be suppression of an antibody response, the suppression of a cytotoxic cellular response, or suppression of both responses. In a preferred embodiment, the carcinoembryonic antigen family member is carcinoembryonic antigen. The animal is preferably a mammal, most preferably a human.

The invention is also directed to compositions and pharmaceutical compositions comprising one or more CEA family members with an altered cellular immunosuppressive region such that the composition when used as a vaccine or immunogen is capable of eliciting an effective humoral and/or cellular immune response against the CEA family member, without the immunosuppressive activity contributed by the cellular immunosuppressive region of the CEA family member. Alterations of the region are exemplified above, but are not so limiting. Preferably, the CEA family member is carcinoembryonic antigen. The composition may further comprise a pharmaceutically-acceptable carrier, excipient, or diluent.

In a further aspect, the invention is directed to a method for effectively immunizing an animal against a tumor that is expressing a carcinoembryonic antigen family member by at least immunizing the animal with a carcinoembryonic antigen family member together with an agent capable of inhibiting a cellular immunosuppressive region of the carcinoembryonic antigen family member. The agent may be, for example, an inhibitor of the engagement of CD8 with a cellular immunosuppressive region of the carcinoembryonic antigen family member, such as a monoclonal antibody such as B9 or L12, or a CD8 peptide or CD8 fusion peptide capable of binding to the immunosuppressive epitope on a CEA family member. It also may be an inhibitor of the engagement of CD1d with a region of the carcinoembryonic antigen family member. Non-limiting examples of a CD8 peptide or fusion peptide include a CD8-Fc fusion peptide or a CD8 peptide comprising an epitope recognized by any one of antibodies OKT8B, OKT8E, OKT8F or OKT8I1. The monoclonal antibodies are preferably humanized monoclonal antibodies. Preferably the animal is a mammal, most preferably a human.

In still yet a further aspect, the invention is also directed to a method for enhancing the immunogenicity of an orally-delivered immunogen in an animal by at least co-administering the orally-delivered immunogen with an agent capable of inhibiting the cellular immunosuppressive activity of a carcinoembryonic antigen family member. In one embodiment, the agent is a monoclonal antibody capable of disrupting the engagement of a carcinoembryonic antigen family member with CD8 or CD1d, such as but not limited to monoclonal antibodies B9 or L12, or a CD8 peptide, CD8 fusion peptide, CD1d peptide or CD1d fusion peptide capable of binding to the immunosuppressive epitope on a CEA family member, or a CD1d peptide or CD1d fusion peptide capable of inhibiting the interaction of a CEA family member with CD1d. Non-limiting examples of such CD8 peptides and CD8 fusion peptides include a CD8-Fc fusion peptide or a CD8 peptide comprising an epitope recognized by any one of antibodies OKT8B, OKT8E, OKT8F or OKT8I1. A humanized monoclonal antibody is preferred. The enhanced immunogenicity may be a humoral, cellular, or both responses.

In yet still a further aspect of the invention, a method is provided for suppressing a humoral or cellular response to an antigen by providing at the site of the antigen a carcinoembryonic antigen, a carcinoembryonic family member, or a fragment, insertion, or fusion polypeptide of CEA or a CEA family member comprising the cellular immunosuppressive region, such that any potential immune response elicited by the antigen may be suppressed by the presence of the activity of the cellular immunosuppressive region of CEA or a CEA family member. Such a region is, for example, the region of CEA depicted in SEQ ID NO:1, or is a region that is recognized by monoclonal antibodies B9 or L12. In a further embodiment of this aspect of the invention, a protein comprising the cellular immunosuppressive region of a CEA family member may be introduced by genetic means into a site within the body, such as a cellular mass or tissue, such that expression and secretion of the protein comprising the cellular immunosuppressive region abrogates an immune response. This aspect of the invention is preferably applied to autoimmune diseases, such as but not limited to inflammatory bowel disease, ulcerative colitis, Crohn's disease, lupus, psoriasis, as examples of diseases in which an inappropriate immune response to an endogenous or exogenous antigen is pathogenetic.

It is thus an object of the invention to provide a method for effectively immunizing an animal against a carcinoembryonic-antigen-family-member-expressing tumor by immunizing the animal using an immunogen consisting of the carcinoembryonic antigen family member lacking an active cellular immunosuppressive region or CD1d binding. The active cellular immunosuppressive region includes a monoclonal antibody B9- or L12-recognizing region.

In a preferred embodiment, the active cellular immunosuppressive region is SEQ ID NO:1, SEQ ID NO:2, or SEQ ID NO:3. The aforementioned immunogen may have a deletion, alteration, mutation, or truncation of the active cellular immunosuppressive region which abrogates its cellular immunosuppressive activity. The cellular immunosuppressive activity may be directed to a humoral, or cellular response or both.

The carcinoembryonic antigen family member preferably is carcinoembryonic antigen.

It is another object of the invention to provide a method for effectively immunizing an animal against a tumor expressing a carcinoembryonic antigen family member by at least immunizing the animal with the carcinoembryonic antigen family member together with an agent capable of inhibiting a cellular immunosuppressive region of the carcinoembryonic antigen family member. The agent may be a ligand of the cellular immunosuppressive region, such as but not limited to a monoclonal antibody such as B9 or L12. The agent may be an inhibitor of the engagement of CD8 with a cellular immunosuppressive region of a carcinoembryonic antigen family member, or of the engagement of CD1d with a cellular immunosuppressive region of a carcinoembryonic antigen family member. Preferably, the carcinoembryonic antigen family member is carcinoembryonic antigen (CEA), and the mammal a human.

It is a further object of the invention to provide a method for enhancing cellular immunogenicity of an orally-delivered immunogen in an animal by co-administering with the orally-delivered immunogen an agent capable of inhibiting the cellular immunosuppressive activity of a carcinoembryonic antigen family member. The agent may be a ligand of the carcinoembryonic antigen family member capable of disrupting the engagement of the carcinoembryonic antigen family member with CD8 or CD1d, such as but not limited to a monoclonal antibody, such as B9 or L12. The agent is an inhibitor of the engagement of CD8 of CD1d with a cellular immunosuppressive region of the carcinoembryonic antigen family member. Preferably, the carcinoembryonic antigen family member is carcinoembryonic antigen, but it is not so limiting.

It is another object of the invention to provide a method for treating a patient having a carcinoembryonic-antigen-family-member-expressing tumor by at least immunizing the patient with an immunogen consisting of the carcinoembryonic antigen family member lacking a cellular immunosuppressive region. The CEA family member may be lacking a B9/L12 epitope having an alteration, deletion, mutation, or other change which abrogates the cellular immunosuppressive activity of the region.

It is yet another object of the invention to provide a method for suppressing a humoral or cellular immune response in a mammal to an antigen by at least administering to a site of the humoral or cellular response in the mammal an agent comprising a cellular immunosuppressive region of a carcinoembryonic antigen family member. The agent comprising a cellular immunosuppressive region of a carcinoembryonic antigen family member may be carcinoembryonic antigen, a carcinoembryonic antigen family member, or a fragment or fusion polypeptide of either of the foregoing comprising a cellular immunosuppressive region. The administering may be by introducing a vector capable of inducing expression of said agent in cells of said mammal. Preferably, the mammal is a human, and the carcinoembryonic antigen family member is carcinoembryonic antigen. This method is useful for the treatment of chronic inflammatory and autoimmune disorders.

It is still yet another object of the invention to provide pharmaceutical compositions for eliciting an effective immune response to a carcinoembryonic antigen family member comprising an immunogen consisting of the carcinoembryonic antigen family member lacking an active cellular immunosuppressive region. The cellular immunosuppressive region may be a monoclonal antibody B9- or L12-recognizing region, such as SEQ ID NO:1, SEQ ID NO:2, or SEQ ID NO:3. The lacking may be achieved by a deletion, alteration, mutation, or truncation of the active cellular immunosuppressive region. Preferably, the carcinoembryonic antigen family member is carcinoembryonic antigen.

These and other aspects of the invention will be apparent from the following figures and the ensuing detailed description of the invention.

BRIEF DESCRIPTION OF THE DRAWINGS

FIG. 1 shows the homology between a sequence of an antigen that binds to monoclonal antibody B9 and various CEA family members. Amino acid sequence LTIESTPFNVAEGK is designated SEQ ID NO:4; amino acid sequence LLLVHNLPQXXF is designated SEQ ID NO:5; and amino acid sequence LTIESTPFNVAEGKEV LLLVHNLPQHLF is designated SEQ ID NO:6.

FIG. 2 shows that transfected, GFP-CEA-expressing 293T cells are recognized by monoclonal antibody B9.

FIG. 3A-B show that mAb B9 and mAb L12 reactivity were both isolated to the N domain, specifically within the loop formed by the sequence GYSWYKGERVDGNRQII (SEQ ID NO:1) (FIG. 3A); and that a sugarless mutant transfectant was still capable of being stained with mAb B9 (FIG. 3b).

FIGS. 5A-B shows that mAb B9 recognized other CEA family members: CEACAM6(NCA), CEACAM1-4L and CEACAM8 (CGM6) transfectants. The CEA subfamily members recognized by B9 share the B9 epitope in the N domain either exactly or with minor modification. As indicated FIG. 3A, mAb B9 recognizes GYSWYKGERVDGNRQII (SEQ ID NO:1) in CEA, and WYKGER/DGNR (SEQ ID NO:7); WYKGER/DGNS (SEQ ID NO:8); and WYKGER/DANR (SEQ ID NO:9) in related family members.

DETAILED DESCRIPTION OF THE INVENTION

Figure 3B:
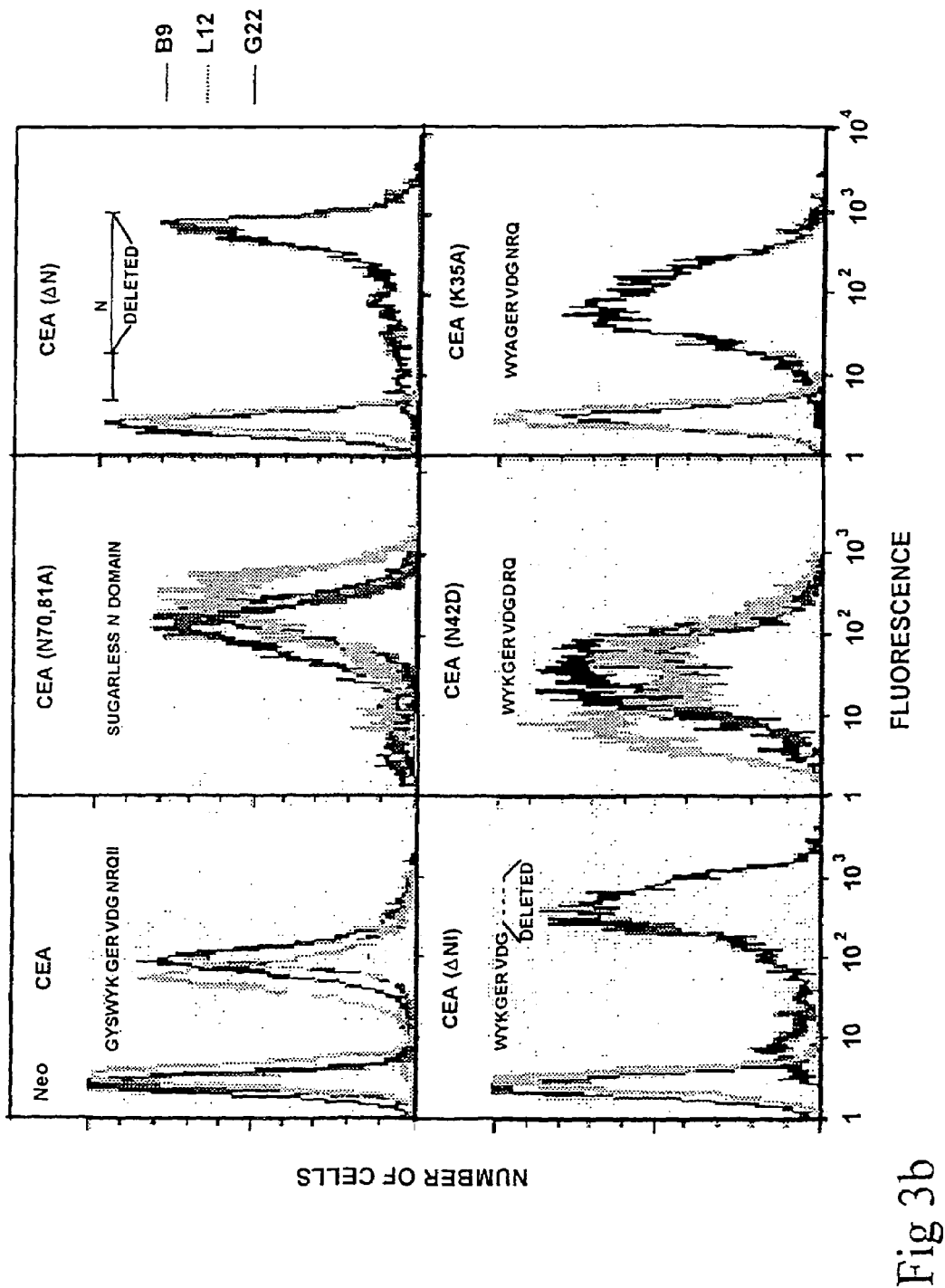

The present inventors, in further studies of the intestinal epithelial cell glycoprotein gp180, have identified it as the oncofetal antigen known as carcinoembryonic antigen, or CEA. The attribution of the characteristics of gp180 to CEA, and the recognition that CEA is naturally expressed on intestinal epithelial cells, offers several new modalities for both improvements of mucosal vaccination in general, as well as a means for improving the immunogenicity of CEA, a popular yet seemingly recalcitrant target for immunotherapy for cancers that overexpress CEA. Moreover, as other CEA family members share common aspects with gp180, now recognized to be CEA, immunotherapetic approaches using other CEA family members, such as cancer immunotherapy, may also be enhanced.

In the aspect of the invention directed to enhancing the immune response specifically to CEA and its family members, the invention herein provides an explanation for the poor immunogenicity elicited by CEA in various cancer immunotherapy trials that have been performed to date, and offers a means for rectifying the poor immunogenicity. The inventors herein have identified an epitope of CEA extending from amino acids 30 to 46, GYSWYKGERVDGNRQII (SEQ ID NO:1), against which monoclonal antibodies raised thereto block the cellular immunosuppressive activity of CEA. Specifically, monoclonal antibodies B9 and L12, which recognize the epitopes WYKGERV (SEQ ID NO:2) and YKGERVD (SEQ ID NO:3), respectively, when included in an IEC:T cell culture, block the cellular immunosuppressive activity of CEA. Thus, elimination of the aforementioned epitope in vaccines or other immunogens against which an immune response to CEA is desired will avoid the cellular immunosuppressive activity of CEA and allow an effective anti-CEA cellular response to be elicited. Such an effective CEA immunogen may be achieved using fragments of CEA exclusive of the aforementioned cellular immunosuppressive region, or a fusion polypeptide which deletes the cellular immunosuppressive region from the CEA molecule.

The cellular immunosuppressive region of CEA or of a CEA family member is defined herein as a region: 1) that binds to CD8 and alters signaling such that cytotoxic T cells are not generated and 2) that activates regulatory or suppressor T cells which mediate immunosuppression. The latter activity is mediated by the interaction between a CEA family member and the class 1b molecule CD1d. Either or both of these activities may be suppressed, or enhanced, by the methods and agents of the invention.

The aforementioned strategies in achieving an effective cellular immune response against CEA, for the treatment of CEA-expressing cancers, may also be translated to other CEA family members, such as NCA, CGM-2, CGM6 and BGP, or, using newly-adopted nomenclature, CEACAM6, CEACAM7, CEACAM8 and CEACAM1, respectively; or, to other molecules expressing the B9/L12 epitopes described herein, for the treatment of cancers in which these CEA family member proteins are expressed and are thus targets for cancer immunotherapy.

In a further embodiment of the invention, agents and methods are provided for the treatment of CEA-expressing tumors beyond the methods described above, in which a more effective CEA vaccine is provided. The results presented here provide an explanation for the immunosuppression associated with these tumors. Moreover, increased expression of CEA in conjunction with any other tumor antigen explains the failure of the immune system to identify the appearance of such other tumor antigens. Thus, upon identification of the increased expression of CEA in any dysproliferative disease, a cause for general cellular immunosuppression is identified, and therapies to enhance a cellular response in the presence of the cellular immunosuppressive CEA may be initiated, as described herein, to elicit an effective cellular response. As will be seen below, gp180/CEA does not inhibit the effector function of cytotoxic T lymphocytes, so that if the therapies described herein successfully elicit a cellular immune response against the target antigen, be it CEA or another antigen, the effector cells will carry out their cytolytic activity against cells expressing the antigen.

As alluded to above, the invention extends beyond therapeutic modalities to enhance the immunogenicity of CEA and avoid a cellular immunosuppressive response. The identification of gp180 as CEA, in combination with the recognition that intestinal epithelial cells are antigen presenting cells, that CEA engages CD8 resulting in suppression of a cytotoxic T cell response, and that CEA activates a T suppressor cell response by association of gp180/CEA with CD1d as described in Campbell et al., 1999, J. Biol. Chem. 274:26259-26265, incorporated herein by reference in its entirety, provides a new means for enhancing the immunogenicity, particular of a cellular response, against any antigen, immunogen or vaccine that is presented by gp180/CEA-bearing or -expressing cells, such as intestinal epithelial cells. In a particular embodiment, such vaccines delivered mucosally, i.e., oral vaccines, may not elicit a desirably robust cellular immune response thereto for the reasons mentioned above and the invention is directed to oral vaccination in conjunction with a means for blocking the cellular immunosuppressive effects of gp180/CEA. While Applicants are not bound to theory, the finding of the immunosuppressive effects of gp180/CEA on CD8+ T cells and that CD1d restricted T cells inhibit other immune responses, the attendant inhibition of a cytotoxic T-cell response, and/or activation of T-suppressor cells, and their heretofore unknown and now surprising correlation with CEA, may be advantageously used in avoiding such immunosuppressive activities by the means described herein. Such means, as mentioned above, include co-administration of an agent which blocks the cellular immunosuppressive region of CEA, antibodies which bind to and block the cellular immunosuppressive activity of CEA, and other agents which block signalling resulting from the engagement of CD8 or CD1d with the aforementioned region of CEA. These are merely non-limiting examples of methods and agents which may be used to abrogate oral tolerance during desired immunization protocols.

Furthermore, in certain instances, immunosuppression is desirable, such that the cellular immunosuppressive region of a CEA family member is a useful activity. For example, in autoimmune diseases and other undesired or inappropriately robust immune responses, methods for abrogating a humoral and/or cellular immune response are desirable. For example, in various inflammatory bowel diseases such as ulcerative colitis and Crohn's disease, as well as other localized and systemic autoimmune diseases including lupus and psoriasis, an undesired immune response exists, and flare-up of the disease has an immunological basis. In accordance with the present invention, use of a CEA family member which has an active cellular immunosuppressive region, or a truncation, fusion polypeptide, or other agent with the properties of the aforedescribed region of various CEA family members is useful for local or systemic therapy, disease dependent, for abrogating a humoral or cellular immune response. A congenital or acquired absence of CEA or CEA family member is believed to promote chronic inflammation; gene therapy to the affected cellular population or tissue provides a means for providing or increasing the production of CEA or CEA family member and the attendant and desirable, in this instance, suppression of a humoral and/or cellular response.

The preferred carcinoembryonic antigen family member immunogens for use in a vaccine for eliciting a cellular response to the carcinoembryonic antigen family member are modified to lack an active region of the carcinoembryonic antigen family member molecule wherein CD8 or CD1d engagement occurs. In the case of carcinoembryonic antigen, the area is shown generally in SEQ ID NO:1, and more specifically as SEQ ID NO:2, the epitope recognized by monoclonal antibody B9. Thus, a preferred CEA immunogen is lacking SEQ ID NO:1 or SEQ ID NO:2. The lacking of the region may be achieved by partial or total deletion, alteration of a critical amino acid which confers activity, substitution with another sequence to preserve the desired immunogenicity of the remainder of the molecule, formation of a fusion polypeptide or truncated molecule, all of which abrogate the cellular immunosuppressive activity of the CEA family member. A skilled artisan, based on understanding the present invention and the immunological activity conferred by the region of CEA identified herein, will readily design molecules without the activity. Corresponding deletions of related carcinoembryonic antigen family members are also embraced herein for use as immunogens or compositions in vaccines for the aforementioned uses.

In the instance where the cellular immunosuppressive region is desired, agents such as the immunosuppressive peptide portion of the CEA family member, or fusion polypeptides, may be provided which offer the activity of decreasing the immune response.

The foregoing modified carcinoembryonic antigen family member for use as a vaccine may be administered to an animal patient, preferably a mammalian patient, and most preferably a human patient, by routine methods known to elicit a cellular response for immunogens that normally elicit a cellular response. A preferred but non-limiting route is oral, mucosal, intradermal, intramuscular or subcutaneous. The immunogens of the invention lacking the activity of the cellular immunosuppressive region elicit a therapeutic or protective cellular response and thus are capable of an antibody or cytotoxic activity against cells expressing the carcinoembryonic antigen family member.

In a further aspect, the cellular response of an orally- or mucosally-delivered immunogen other than a carcinoembryonic antigen family member may be enhanced by blocking the cellular immunosuppressive activity of a carcinoembryonic antigen family member, preferably carcinoembryonic antigen, during antigen presentation. Agents which disrupt the engagement of the T cell CD8 molecule and the cellular immunosuppressive region of the carcinoembryonic antigen family member, or block the association of the carcinoembryonic antigen family member with CD1d are co-administered to block the effect. The co-administered agent may be administered by the same route or a different route than the immunogen, to provide effective blockage of the cellular immunosuppressive effect. For example, a small-molecule antagonist of the carcinoembryonic antigen family member-CD8 interaction may be included in the oral vaccine, or may be administered parenterally to the individual. In another embodiment, an agent capable of disrupting the signalling events following carcinoembryonic antigen family member-CD8 engagement may be administered.

As noted above, carcinoembryonic antigen family member deletion mutants useful for eliciting a cellular immune response are embraced herein. Such deletion mutants, or fragments lacking the cellular immunosuppressive region, may be prepared by routine methods and then screened for successful elimination of cellular immunosuppression in an in-vivo assay. These assays for effective induction of a CTL response are routine and readily undertaken by one skilled in the art.

Candidate patients or individuals for the therapeutic and protective therapies of the invention include animals, preferably mammals including livestock and domestic animals, and most preferably humans. While the expression of various CEA family members among non-human mammalian species has been little studied, the teachings herein are applicable notwithstanding the member(s) of the family expressed in a particular species. One target patient population for the methods herein is that with a carcinoembryonic antigen family member-expressing tumor in which control or eradication of the tumor is desired. Traditionally, carcinoembryonic antigen family member immunogens have been unsuccessful at mounting an effective cellular response, now understood based on the present invention to be the presence of a cellular immunosuppressive epitope amongst the carcinoembryonic antigen family member epitopes. The epitope appears responsible for both suppression of CD8 signalling and the induction of cytotoxic T cells, as well as activation of T cells with suppressor activity. In another embodiment, the cellular immune response to another antigen, such as an infectious disease immunogen or other cancer immunogen, particularly one delivered orally and presented by mucosal cells, may be enhanced by blocking the cellular immunosuppressive activity of the carcinoembryonic antigen family member, particularly carcinoembryonic antigen, now known to be present in intestinal (epithelial) cells and responsible based herein for reducing the effectiveness of immunogens presented thereby. Moreover, the CD8 T-suppressor cells generated by CEA are not target restricted. Vaccines comprising immunogens which enter the immune system through the intestinal epithelial cell are merely exemplary of such vaccines for which an enhanced cellular immune response is achievable by the methods herein.

The invention is also directed to pharmaceutical compositions of the aforementioned CEA family member molecules lacking cellular immunosuppressive activity, and to their use, for example, as an effective immunogen for a CEA family member-expressing tumor. Examples of such altered CEA family member molecules include CEA with an N domain deletion, or a K35A substitution in the N domain, or a deletion of GYSWYK or NRQII. These are described in Taheri, et al., 2000, J. Biol. Chem. 275:26935-43, which is incorporated herein by reference in its entirety. These molecules may be formulated with appropriate pharmaceutically-effective carriers, excipients or diluent for local or systemic administration, as appropriate for the prophylaxis or treatment of a particular disease or condition.

As noted above, previous studies have suggested that normal intestinal epithelial cells can act as nonprofessional antigen presenting cells, selectively activating CD8$^+$ suppressor T cells. As will be shown in the examples below, an epithelial cell surface glycoprotein, initially called gp180, recognized by monoclonal antibodies B9 and L12 was determined to be critical to the activation of these regulatory T cells. Purification and sequence analysis of mAb B9 reactive material revealed sequence homology with carcinoembryonic antigen (CEA). Transfection of CEA cDNA into CHO cells, 293T cells and F01 cells (melanoma line) conferred mAb B9 reactivity to these transfectants. Properties previously attributed to gp180 such as CD8α binding and activation of CD8 associated p56lck could be reproduced using purified CEA from these transfectants. The mAb B9 epitope was determined to be in the N domain characterized by the sequence GYSW-YKGERVDGNRQII (SEQ ID NO:1). This sequence is found with some variation in other CEA subfamily members as well. These data suggest that CEA may be an important immunoregulatory molecule expressed in the normal intestine and that increased expression in malignancy may explain the immunosuppression associated with these tumors.

EXAMPLE 1

Monoclonal Antibody B9 Affinity-purified Material Bears Sequence Homology to CEA Monoclonal antibodies (mAb) B9 and L12 are described in Yio et al., 1997, J. Biol. Chem. 272:12786-92, incorporated herein by reference in its entirety. Two billion T84 cells were lysed with an octyl glucoside based detergent buffer and passed over a mAb B9 affinity column. B9 reactive material was then eluted with 2M glycine (pH 2.8) and concentrated using YM 30 Centricon membranes. mAb B9 reactivity of the eluted and concentrated material was confirmed by Western Blot. The purified material was then subjected to N terminal sequencing by Edman degradation. As seen in FIG. 1, over the first 25 amino acids, there was 100% amino acid sequence homology with CEA and homologies ranging from 65% to 96% with other CEA subfamily members.

EXAMPLE 2

CEA Transfectants Express the B9 Epitope

Given the homology to CEA, it was next determined whether this dominant member of the CEA subfamily expressed the epitopes recognized by mAbs B9 and L12. A CEA-GFP bicistronic construct was transfected into 293T and F01 cells. As seen in FIG. 2 GFP expressing 293T cells co-expressed a molecule recognized by mAb B9. This mAb did not recognize cells which were mock transfected or transfected with GFP alone. Similar data were obtained using F01 cells and by FACS analysis of CHO cell transfectants (see FIG. 3). These data show that CEA expresses the B9 epitope.

Next, a series of CHO cells transfected with full-length CEA cDNA or cDNAs containing mutations in the N or C domain of CEA were analyzed. As seen in FIG. 3a, B9 reactivity was isolated to the N domain, specifically within the exposed loops formed by the sequence GYSW-YKGERVDGNRQII (SEQ ID NO:1). Destruction of this loop structure abrogated mAb B9 activity. mAb L12 recognizes a sequence overlapping the B9 epitope whereas other previously described anti-CEA mAbs B18 and A20 recognize epitopes which are more C terminal to the B9 and L12 epitope. Interestingly, while the initial description of the B9 and L12 reactive material suggested that the epitope recognized by these mAbs required the presence of N-linked sugars (epitope was removed by N-glycanase treatment), a sugarless mutant transfectant was still capable of binding mAb B9 (FIG. 3b).

EXAMPLE 3

CEA Binds to CD8α Chains

Figure 4:
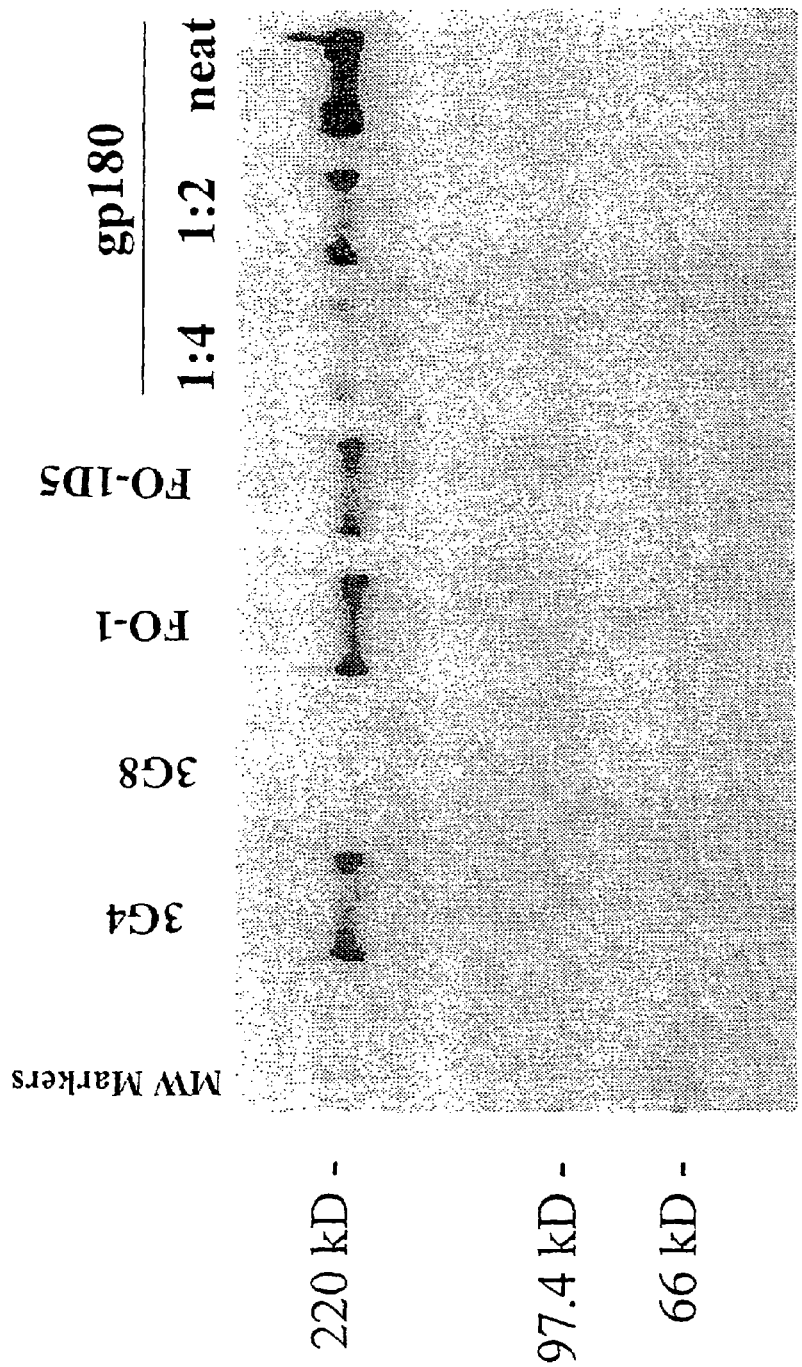
FIG. 4 shows that CEA binds to CD8α chains in that only CD8α but not CD4 transfected hybridoma cells were capable of absorbing B9 reactive material.

CEA exists as a GPI anchored glycoprotein on the surface of IECs. This molecule can be cleaved using the enzyme PIPLC. CEA-GFP transfected 293 T cells were treated with PIPLC and the liberated GPI anchored molecules were used for a series of absorption studies. Murine T cell hybridomas transfected with either human CD4 (3G4) or human CD8α (3G8) cDNA were co-cultured with vector transfected or CEA transfected 293 T PIPLC treated supernatants. Absorption of CEA by either CD4 or CD8 was determined by immunoblotting with mAb B9. As seen in FIG. 4 only CD8α but not CD4 transfected hybridoma cells were capable of absorbing the B9 reactive material. These findings are consistent with functional properties previously ascribed to gp180.

EXAMPLE 4 mAb B9 Recognizes an Epitope on Other CEA Subfamily Members

Figure 5A:
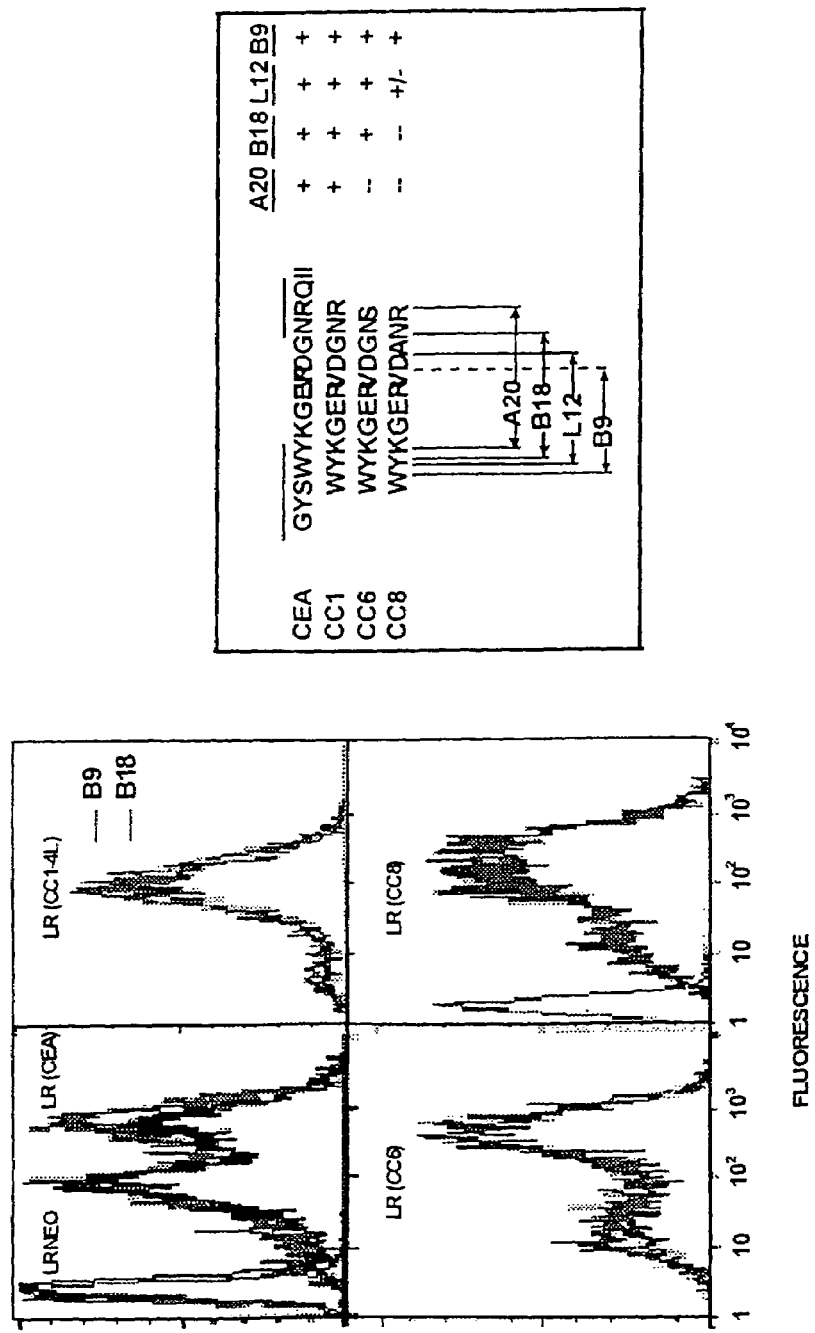

Given the high homology of the N domain in a number of CEA subfamily members, it was next determined whether mAb B9 and L12 had a recognition pattern restricted to CEA. CHO cells transfected with NCA (CEACAM6), BGPa (CEACAM1-4L), BGPx (CEACAM1-1L), CGM2 (CEACAM7), CGM6 (CC8) were stained with mAbs B9 and L12 and analyzed by flow cytometry. As seen in FIG. 5a-b, mAb B9 recognized NCA, BGPa, and CGM6 transfectants but not CGM2. These CEA subfamily members share the B9 epitope in the N domain. These findings suggest that both mAbs are not CEA specific and may indicate distinct functional properties of these different subfamily members.

A novel role for intestinal epithelial cells, that of antigen presenting cells, has been previously established: IECs can take up soluble proteins and present them to T cells. In the normal state such presentation results in the selective activation of CD8$^+$ suppressor T cells. This interaction has been further characterized by identifying two molecules expressed by normal IECs which bind to the TcR and CD8 molecules on these regulatory T cells, CD1d, and a molecule recognized by two anti-epithelial mAbs previously generated by the inventors (B9 and L12), which was referred to as gp180. Both mAbs recognizing gp180 were initially identified in a functional screen. Purified gp180 was shown to be capable of binding to CD8, activating p56 1 ck and of binding to CD1d.

In the foregoing examples, gp180 has been identified as CEA. This was confirmed by sequence analysis, the ability of B9 and L12 to stain CEA transfectants and the ability of CEA to bind to CD8. It is intriguing to note that both mAbs B9 and L12 recognize epitopes that are within 1AA of each other and are associated with a critical functional domain in the CEA molecule. Anti-CEA mAb B18 which recognizes an epitope further C-terminal fails to block p56 1 ck activation in IEC: T cell co-cultures. These studies did not define the domain involved in CD1d complex formation. Since many CEA subfamily members can express the B9 epitope (the CD8 binding domain), their ability to activate distinct suppressor T cell subpopulations may depend upon their ability to bind to different class Ib molecules.

Despite the fact that CEA was identified in 1965 by Gold and Freeman, the functional relevance of this molecule and its associated subfamily members has been poorly understood. The most consistently described function has been one of adhesion and this property has been suggested to help explain its role in tumor metastasis. The inventors here have described an important and heretofore unrecognized immunoregulatory role for CEA in a very specific fashion. It is intriguing to speculate that as CEA expressing adenocarcinomas grow and enhance their expression of CEA, the ability of this molecule to participate in the activation of $CD8^+$ suppressor T cells may allow for the tumor to escape immunologically mediated destruction. Another CEA subfamily member CEACAM1 (BGP) is expressed on a number of other cell types including T cells. CEACAM1 (BGP) has a transmembrane anchor and it contains an ITIM motif in its intra-cytoplasmic trail. As such, binding of CEACAM1 may transmit negative signals to cytotoxic T cells blocking their ability to kill targets. Since CEA subfamily members bind together by both homotypic and heterotypic interactions it is also conceivable that CEA expressed by adenocarcinomas bind to CEACAM1 and CD8 delivering two negative signals to the T cell; blocking cell mediated cytolysis and tumor killing.

Figure 6A:
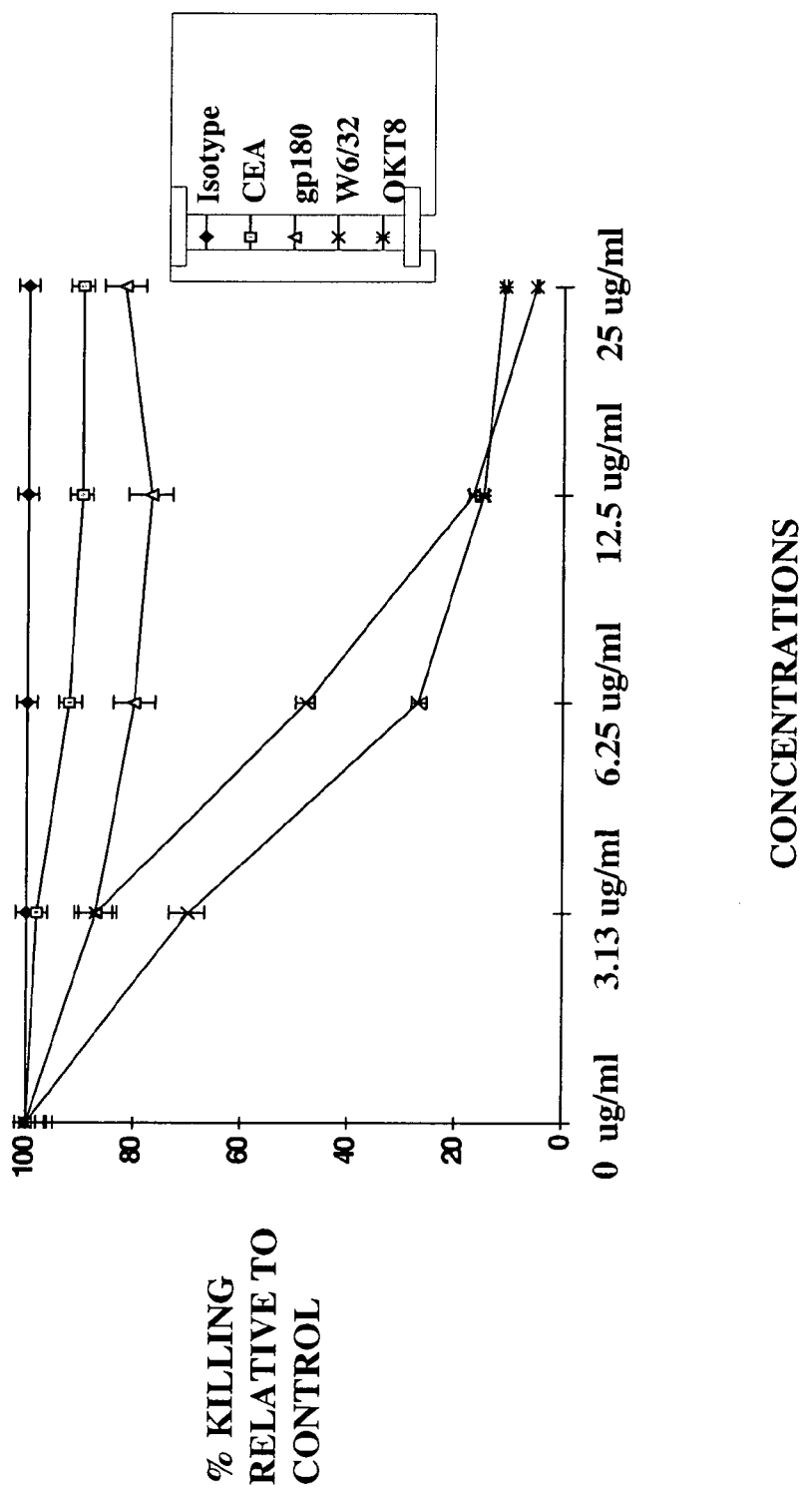
FIGS. 6A-B show, using increasing amounts of purified gp180 (CEA) added to a CTL assay testing alloreactive CTL that, unlike mAbs to MHC class I or CD8 α which both inhibited CTL activity, gp180 induced only a modest decrease (<15% in 3 experiments) in killing (FIG. 6A). In contrast, when varying concentrations of purified gp180 were added to cultures where CTLs were induced, there was complete inhibition of generation of CTLs (FIG. 6B).
Figure 6B:
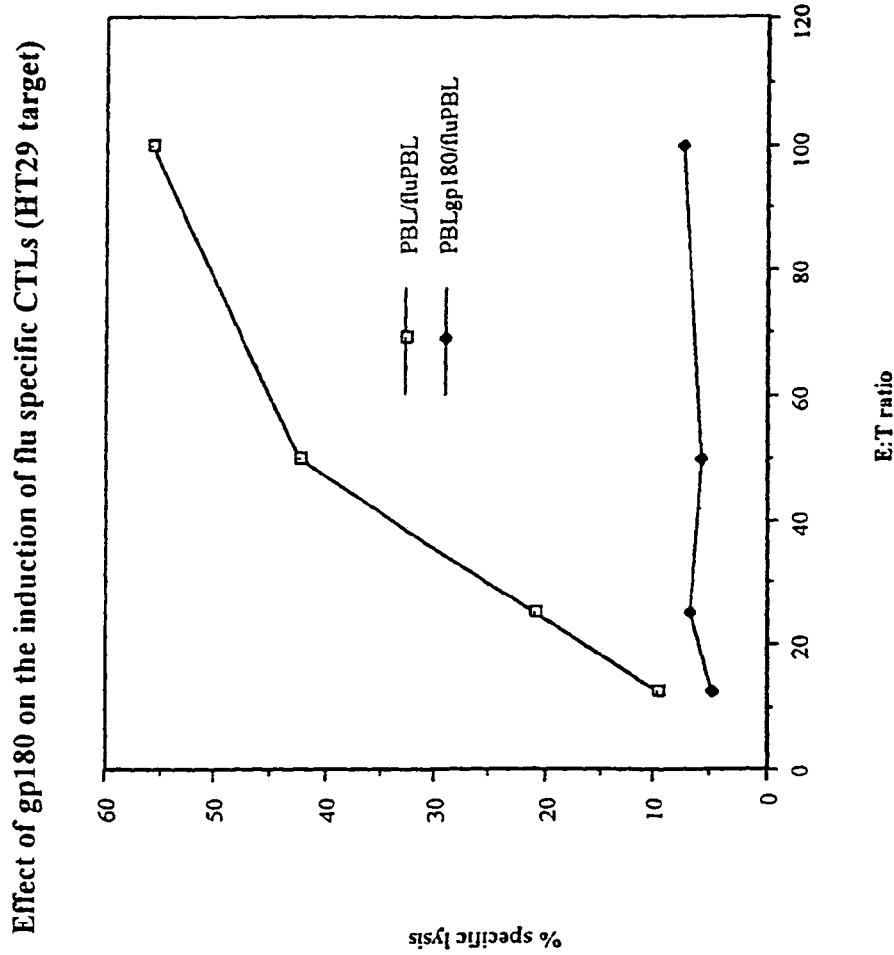

EXAMPLE 5 gp180 Inhibits the Generation of CTLs but Fails to Inhibit their Effector Function The engagement of CD8 by gp180/CEA has been shown to utilize nonoverlapping sites to those used by MHC class I molecules. To address this more directly, increasing amounts of purified gp180 were added to a CTL assay testing alloreactive CTL (generated in mixed lymphocyte reactions) activity against their target. As seen in FIG. 6a, unlike mAbs to MHC class I or CD8α which both inhibited CTL activity, monoclonal antibody B9 affinity purified gp180 induced only a modest decrease (<15% in 3 experiments) in killing, comparable to a CEA (non-monoclonal-antibody-B9-binding) control glyco-protein. In contrast (FIG. 6b), when varying concentrations of purified gp180 were added to cultures where CTLs were induced, there was complete inhibition of the generation of CTLs. The inhibition was only seen when gp180/CEA was added to these cultures within the first 24 hours of co-culture. Addition of gp180 did not affect cell number or viability of the cells in culture. These data indicate that gp180/CEA is altering early events involved in the generation of CTLs.

It was determined next whether similar effects could be seen in anti-viral CTL generation. PBMNC were infected with influenza strain Beijing and co-cultured with freshly isolated autologous peripheral blood T cells (PBT) in the presence or absence of varying concentrations of gp180/CEA. These cultures were maintained for 5 days, at which time virus activated T cells were incubated with influenza infected or uninfected autologous target cells (PHA stimulated T cell blasts). Consistent with the findings seen in FIG. 6, complete inhibition of CTL generation was seen when the priming cultures included gp180/CEA.

Figure 7A:
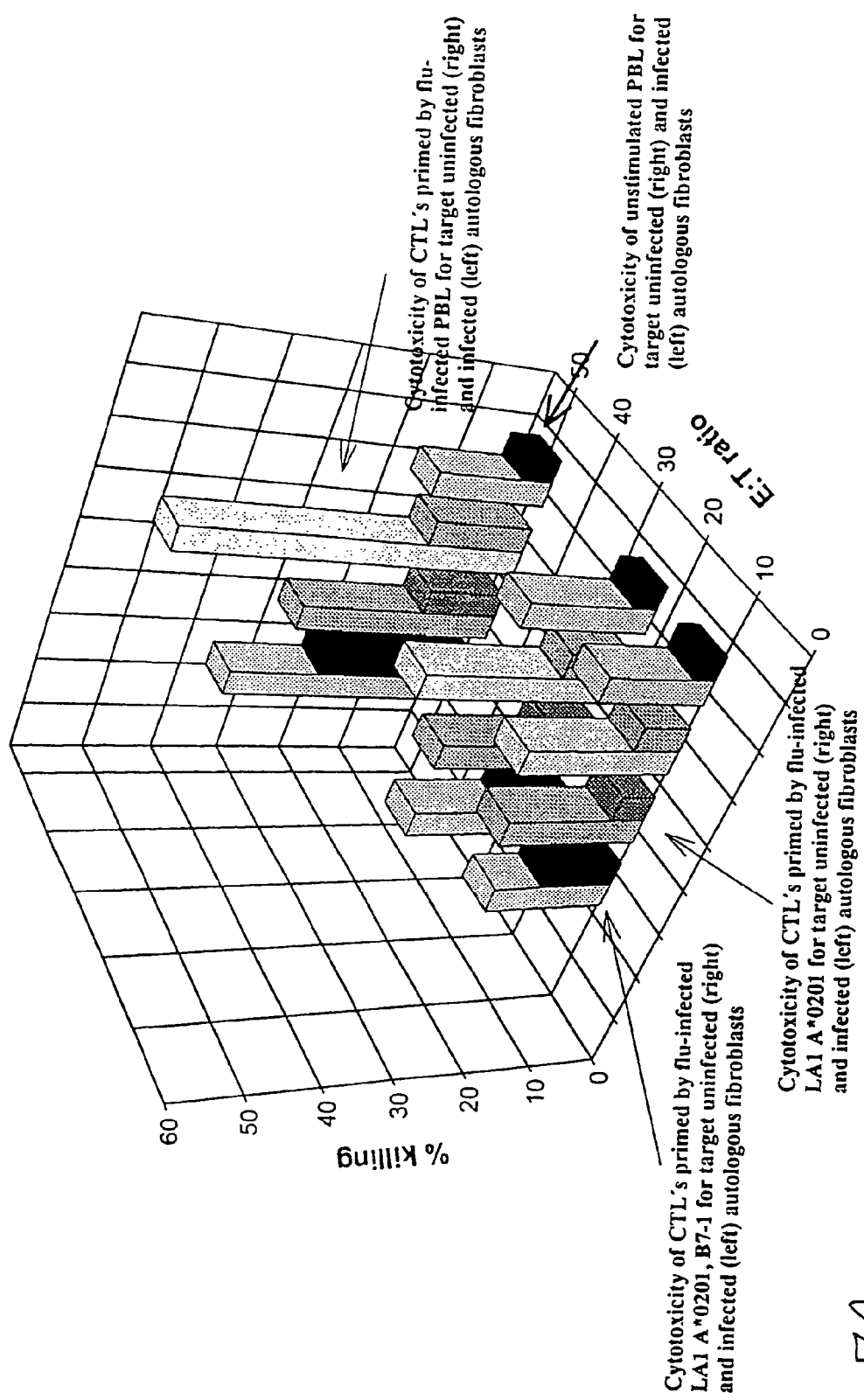
FIG. 7A-B shows that an A2 expressing B cell line and autologous MNC primed for a CTL response whereas the A2 expressing, gp180 expressing HT29 cells did not.
Figure 7B:
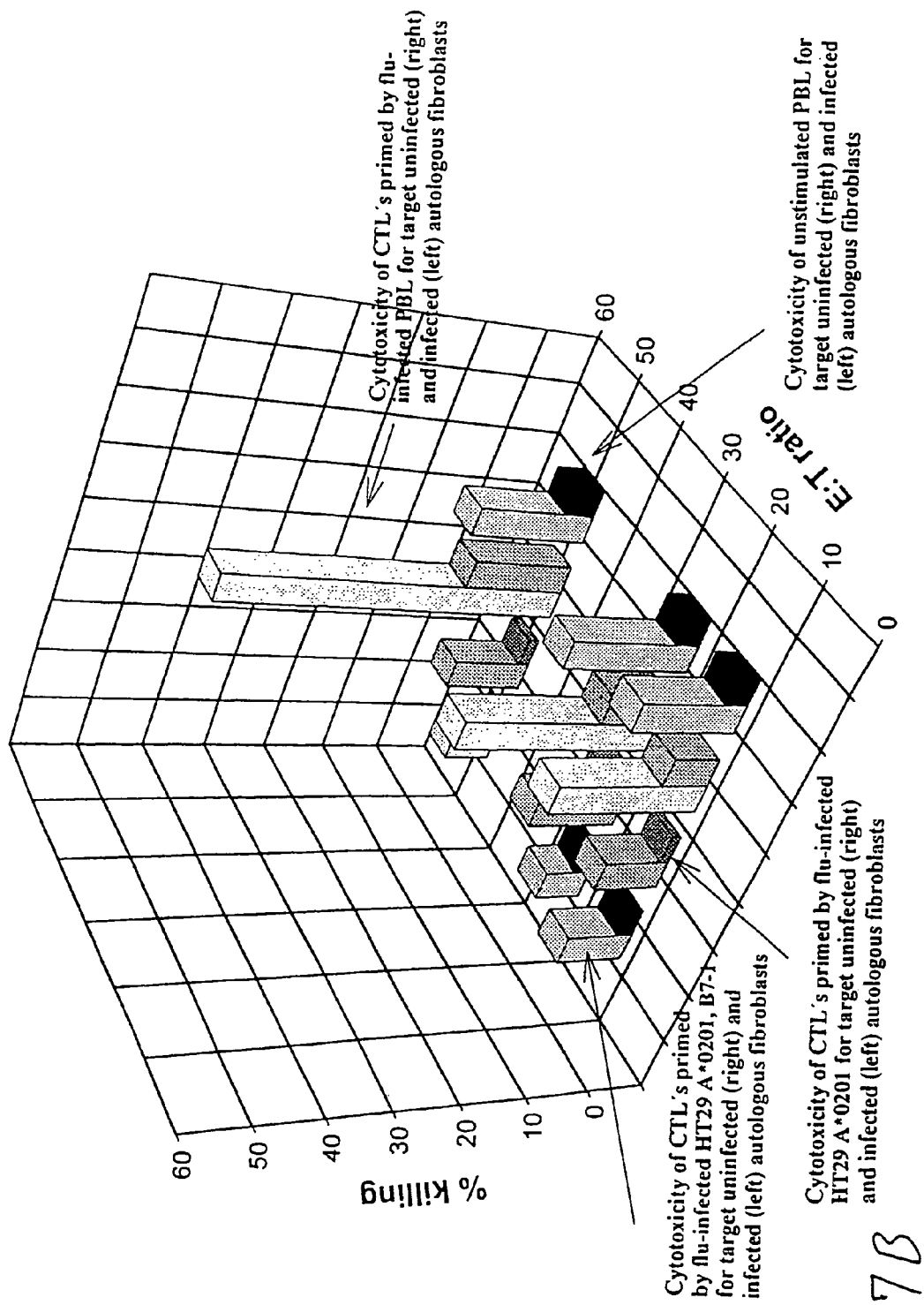

HT29 cells, a human colon cancer cell line, have been reported to be a target for LAK cells. Thus this line can be killed by cytolytic T cells. HT29 constitutively expresses gp180/CEA. Therefore, it was determined whether HT29 cells could prime an anti-influenza CTL response. HT29 cells were transfected with HLA-A2 using a retroviral construct. PB T cells from an HLA-A2+ donor were co-cultured with either an influenza infected or uninfected HLA-A2 expressing B cell line, autologous PBMC or the A2 transfected HT-29 cells. Infection was confirmed in all cells by flow cytometry using an anti-HA specific mAb. After 5 days of co-culture, T cells were incubated with autologous flu infected target cells and killing was assessed. In the absence of influenza infection, no spontaneous killing was seen. Both the A2 expressing B cell line and autologous MNC primed for a CTL response whereas the A2 expressing HT29 cells did not (FIG. 7a). The absence of priming by the HT29 cells did not necessarily reflect the expression of gp180/CEA alone. Intestinal epithelial cells fail to express a number of co-stimulatory molecules which might be important in the generation of CTL. B7-1 (CD80) cDNA was therefore transfected into HT29 HLA-A2 transfectants and their ability to prime a flu specific CTL response was determined. As seen in FIG. 7b while there was restoration of CTL activity there was no evidence of Ag specificity. HLA-A2+ T cells killed both the infected and noninfected cells with similar efficiency. These findings were consistent with the activation of LAK cells rather than class I restricted CTLs.

EXAMPLE 7 gp180/CEA Alters the Signaling Pathway within CTLs

Figure 8A:
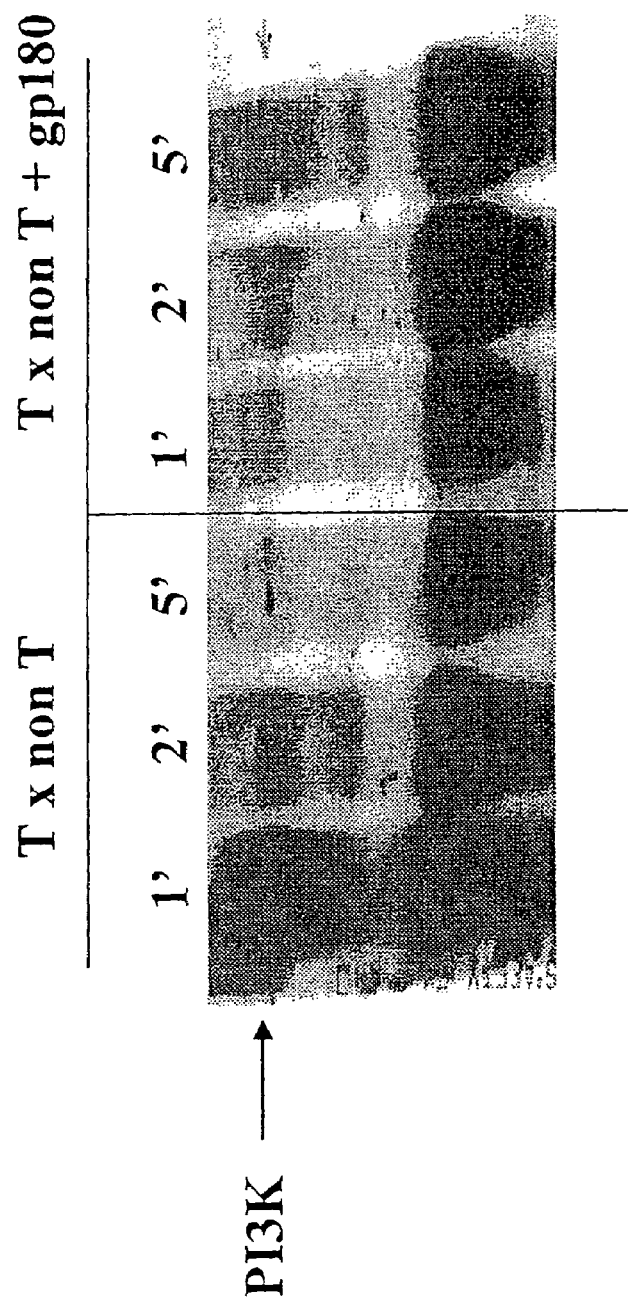
FIGS. 8A-B shows that co-culture of PB T cells with allogeneic adherent cells (DCs, monocytes) resulted in both phosphorylation of PI3K and Vav. Addition of gp180 inhibits PI3K phosphorylation and enhances the kinetics of phosphorylation of vav.
Figure 8B:
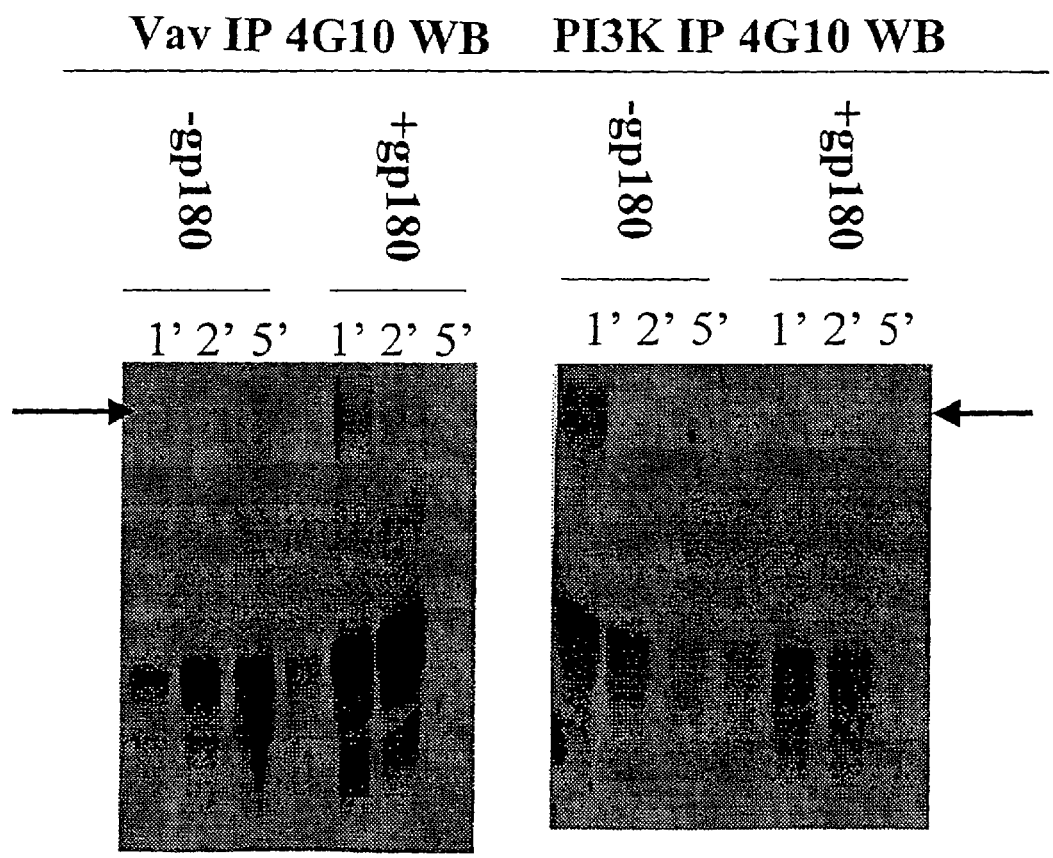

Since gp180/CEA does not appear to inhibit the ability of CD8 to engage class I molecules, the mechanism underlying the inhibition seen was investigated. Previous studies by the present inventors had shown that engagement of CD8 by gp180/CEA results in the rapid autophosphorylation of the CD8 associated src-like kinase p56lck but not the TcR associated kinase p59fyn. In contrast, intact epithelial cells co-cultured with PB T cells induce phosphorylation of both lck and fyn, reflecting the engagement of the TcR by CD1d and CD8 by gp180/CEA. Downstream substrates and kinases are phosphorylated as well including the guanosine exchange factor Vav which is phosphorylated rapidly after gp180/CEA: T cell co-culture. Previous studies have documented a significant role for PI3K and PLCγ1 as well as Vav in the activation of class I restricted CTLs. Given the rapid kinetics of Vav phosphorylation in either IEC: T cell co-cultures or in T cell: gp180/CEA co-cultures, it was determined whether there was an alteration in signaling that would account for gp180/CEA's ability to inhibit CTL generation. As seen in FIG. 8a co-culture of PB T cells with allogeneic adherent cells (DCs, monocytes) resulted in both phosphorylation of PI3K and Vav (and PLCγ1-not shown). In contrast, co-culture of freshly isolated IECs with these same T cells failed to induce PI3K phosphorylation but did induce the phosphorylation of Vav. Confirmation of the role of PI3K in CTL activation came in studies using wortmanin in these same co-cultures. This PI3K inhibitor blocked the generation of alloreactive CTLs but failed to block proliferation of T cells activated by allogeneic epithelial cells. Given these findings, it was necessary to determine whether gp180/CEA had the capacity to alter PI3K phosphorylation. As seen in FIG. 8b, addition of gp180/CEA to T cell: allogeneic adherent cell co-cultures resulted in the loss of PI3K phosphorylation and a brisk upregulation of phospho-Vav. These data indicate that engagement of CD8 by gp180 (CEA) has the capacity to redirect intracellular signaling pathways which may be important in CTL generation.

By the very nature of its co-existence with a sea of antigens one cell layer away from the largest lymphoid organ in the body, the mucosal (intestinal) immune system requires distinct mechanisms to induce and control immune responses. In general, the immunologic tone of the GI tract is one of tight regulation and suppression of immune responses. A variety of factors are likely to be involved in this process. The lymphoid populations present in the GI tract are unique, being resistant to signals mediated through the antigen receptor and exquisitely responsive to co-stimulatory pathways. Professional APCs in the mucosa lack conventional receptors (e.g. CD14) and their ability to stimulate immune responses is modest. Given the location of the intestinal epithelial cells between the antigen-laden intestinal lumen and the cell rich lamina propria, several groups have proposed a novel function for these cells, that of nonprofessional APC. Indeed various investigators have documented the ability of IECs to either activate class II restricted memory cells or class 1b restricted suppressor/regulatory T cells. These latter cells are CD8+ $CD28^{+\ or\ -}$ IL-2R$^+$ and for the most part appear to recognize CD1d as their restriction element. The nature of the antigen presented by this class Ib molecule has not as yet been defined. The activation of these class Ib restricted suppressor cells has been shown to be dependent upon the activation of protein tyrosine kinases including p56 l ck and p59fyn. However, the expression of CD1d alone does not totally account for activation of these cells. A molecular chaperone, a membrane glycoprotein called gp180, is a key component of these interactions. gp180/CEA binds to CD8 and activates CD8 associated p56 l ck. mAbs to gp180/CEA (mAb B9 and L12) block the proliferation and l ck activation in T cells induced by IECs.

In the foregoing examples, the role of gp180/CEA was assessed in the modulation of responses which might promote inflammation. In this context it is interesting to note that, while enteric viral infections occur in class I-expressing IECs, generalized cytolysis of the epithelium or even selected areas of ulceration do not occur in the course of these infections. This finding documents that gp180/CEA is capable of inhibiting CTL generation without affecting cell viability or numbers. However, the expression of gp180/CEA by itself does not render targets resistant to lysis. Therefore, were anti-viral CTLs to be generated elsewhere, there is potential for those cells to lyse epithelial targets.

The effect of gp180/CEA on CTLs may be only one of several mechanisms whereby this molecule participates in maintaining controlled inflammation or immunological unresponsiveness in the gut. As alluded to earlier, gp180/CEA is a key component in the generation of class 1b restricted regulatory T cells. Activation of these cells would add further to controlled inflammation.

The mechanism whereby gp180/CEA blocks CTL generation is also of interest. Previous studies have defined a post receptor pathway for all cytolytic cells which includes PI3K and Vav. By mechanisms which remain to be defined, co-incubation of T cells with gp180/CEA results in the absence of PI3K phosphorylation and the rapid and robust phosphorylation of Vav. This appears to correlate with the alteration in T cell function. Such a phenomenon is not without precedent as the presence or absence of other co-stimulatory molecules (e.g. B7-1, B7-2) have profound effects on the nature of the T cell response. Interestingly despite the fact that both class I MHC and gp180/CEA bind to CD8 (albeit at different sites), signals transduced by these two molecules are quite different.

In summary, the foregoing studies have demonstrated that the epithelial glycoprotein gp180, also known as CEA, has the capacity to regulate potentially harmful immune responses. Such a finding underscores the potential role for this molecule in regulating mucosal immune responses. Taken together with clinical observations of the failure of an endogenous cellular immune response to be mountable against antigens or epitopes expressed or over-expressed in certain tumors, the poor immune response elicited when full-length CEA is utilized as an immunogen, and the phenomenon of oral tolerance, the central immunomodulatory role of CEA in these and other instances is clearly a target for modulation in order to overcome the cellular immunosuppression often seen and responsible for failures in an otherwise promising immunotherapeutic approach to the treatment of cancer, as well and in prevention of certain infectious diseases.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated herein by reference in their entireties.

The murine hybridoma cell line L12 was received by the American Tissue Culture Center (ATCC) on Dec. 27, 2007 and the deposit tested and determined to be viable on Mar. 17, 2008. The murine hybridoma cell line B9 was received by the ATCC on Dec. 27, 2007 and the deposit tested and determined to be viable on Mar. 24, 2008. The complete name and address of the depository is as follows: American Tissue Culture Center, 10801 University Boulevard, Manassas, VA 20110-2209 USA.

What is claimed is:

1. A method for immunizing an animal against a tumor expressing a carcinoembryonic antigen comprising immunizing said animal using an immunogen consisting of said carcinoembryonic antigen modified to lack cellular immunosuppressive activity or CD1d binding, wherein said carcinoembryonic antigen comprises an N domain deletion, a K35A substitution in the N domain, or a deletion of GYSWYK (SEQ ID NO: 10) or NRQII (SEQ ID NO: 11).

2. The method of claim 1 wherein said carcinoembryonic antigen modified to lack cellular immunosuppressive activity comprises said carcinoembryonic antigen having a region recognized by monoclonal antibody B9 or L12 modified to inactivate said cellular immunosuppressive activity.

3. The method of claim 2 wherein said region is SEQ ID NO:1, SEQ ID NO:2, or SEQ ID NO:3.

4. A method for immunizing an animal against a carcinoembryonic-antigen-expressing tumor comprising immunizing said animal using an immunogen consisting of said carcinoembryonic antigen having a K35A substitution in the N domain, a deletion of GYSWYK (SEQ ID NO: 10) or a deletion of NRQII (SEQ ID NO: 11).

5. A method for enhancing cellular immunogenicity of an orally-delivered immunogen in an animal comprising co-administering with said orally-delivered immunogen an agent capable of inhibiting the cellular immunosuppressive activity of carcinoembryonic antigen, wherein said agent is a ligand of said carcinoembryonic antigen capable of disrupting the engagement of a carcinoembryonic antigen family member with CD8, disrupting the association of said carcinoembryonic antigen family member with CD1d, or the combination of both.

6. The method of claim 5 wherein said ligand is a monoclonal antibody.

7. The method of claim 6 wherein said monoclonal antibody is B9 or L12.

8. The method of claim 5 wherein said agent is an inhibitor of the engagement of CD8 with a cellular immunosuppressive region of said carcinoembryonic antigen family member, or an inhibitor of the engagement of CD1d with a cellular immunosuppressive region of said carcinoembryonic antigen family member.

9. A method for suppressing a humoral or cellular immune response in a mammal to an antigen comprising administering to a site of said humoral or cellular response in said mammal an agent consisting of SEQ ID NO: 1, SEQ ID NO: 2, or SEQ ID NO: 3 or a fusion polypeptide thereof.

10. The method of claim 9 wherein said mammal is a human.

* * * * *

UNITED STATES PATENT AND TRADEMARK OFFICE
CERTIFICATE OF CORRECTION

PATENT NO. : 7,452,540 B2  
APPLICATION NO. : 10/492571  
DATED : November 18, 2008  
INVENTOR(S) : Lloyd Mayer and Clifford P. Stanners It is certified that error appears in the above-identified patent and that said Letters Patent is hereby corrected as shown below:

In the Specification at column 1, line 3, please add the following paragraph:

--This invention was made with Government support under Grant No. AI023504 awarded by the National Institutes of Health. The government has certain rights in the invention.--

Signed and Sealed this
Thirtieth Day of September, 2014

Michelle K. Lee
*Deputy Director of the United States Patent and Trademark Office*